United States Patent
Reichel et al.

(10) Patent No.: US 6,206,844 B1
(45) Date of Patent: Mar. 27, 2001

(54) REUSABLE ULTRASONIC SURGICAL INSTRUMENT WITH REMOVABLE OUTER SHEATH

(75) Inventors: Lee E. Reichel, Springboro; Jean M. Beaupre, Cincinnati, both of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/344,582

(22) Filed: Jun. 25, 1999

Related U.S. Application Data

(63) Continuation of application No. 08/808,273, filed on Feb. 28, 1997, and a continuation of application No. 08/808,652, filed on Feb. 28, 1997, and a continuation of application No. 08/949,161, filed on Oct. 10, 1997.

(51) Int. Cl.[7] .................................................... A61B 17/00
(52) U.S. Cl. ................................................ 601/2; 600/121
(58) Field of Search ...................... 600/437, 462, 600/464, 439, 121, 459; 601/2, 3, 4; 604/22

(56) References Cited

U.S. PATENT DOCUMENTS

| | | | |
|---|---|---|---|
| 4,492,574 | 1/1985 | Warrin et al. ........................ 433/81 |
| 4,634,420 | 1/1987 | Spinosa et al. ..................... 604/22 |
| 5,038,756 | 8/1991 | Kepley ................................ 128/24 |
| 5,135,001 | * 8/1992 | Sinofsky et al. ............... 128/662.06 |
| 5,255,669 | * 10/1993 | Kubota et al. ....................... 128/24 |
| 5,322,055 | 6/1994 | Davison et al. ....................... 601/2 |
| 5,353,783 | * 10/1994 | Nakao et al. ........................ 128/4 |
| 5,382,228 | * 1/1995 | Nita et al. ........................... 604/22 |
| 5,391,144 | * 2/1995 | Sakurai et al. ...................... 604/22 |
| 5,398,689 | * 3/1995 | Connor et al. ................. 128/662.03 |
| 5,449,370 | 9/1995 | Vaitekunas ......................... 606/169 |
| 5,469,853 | * 11/1995 | Law et al. ..................... 128/662.06 |
| 5,474,071 | 12/1995 | Chapelon ........................... 128/660 |
| 5,678,551 | 10/1997 | Stevens . |
| 5,810,859 | 9/1998 | DiMatteo et al. .................. 606/169 |
| 5,817,015 | * 10/1998 | Adair ................................. 600/121 |
| 5,897,523 | * 4/1999 | Wright et al. ........................ 604/22 |
| 5,931,788 | * 8/1999 | Keen et al. ......................... 600/462 |
| 6,022,362 | * 2/2000 | Lee et al. ........................... 606/159 |

OTHER PUBLICATIONS

The Harmonic Scalpel® 10 mm Assembly Instructions, UltraCision Incorporated.

* cited by examiner

*Primary Examiner*—Marvin M. Lateef
*Assistant Examiner*—Eleni Mantis Mercader

(57) ABSTRACT

The present invention is directed to an ultrasonic surgical instrument including an improved outer sheath which is removable and which rotateably engages the ultrasonic waveguide to facilitate attachment of the ultrasonic instrument to a handpiece. In particular, in one embodiment of the present invention, an improved sheath includes a first and second sheath pin slots extending from the proximal end of the sheath to first and second sheath pinholes respectively. An ultrasonic surgical instrument according to the present invention further includes a connector pin, the connector pin extending through the first sheath pinhole, a waveguide pinhole and the second sheath pinhole and an attachment hub surrounding the outer sheath, wherein the attachment hub is slideable over the outer sheath. A first pin slot may be positioned on an inner surface of the attachment hub wherein the connector pin engages the first pin slot when the attachment hub is in its proximal most position.

21 Claims, 4 Drawing Sheets

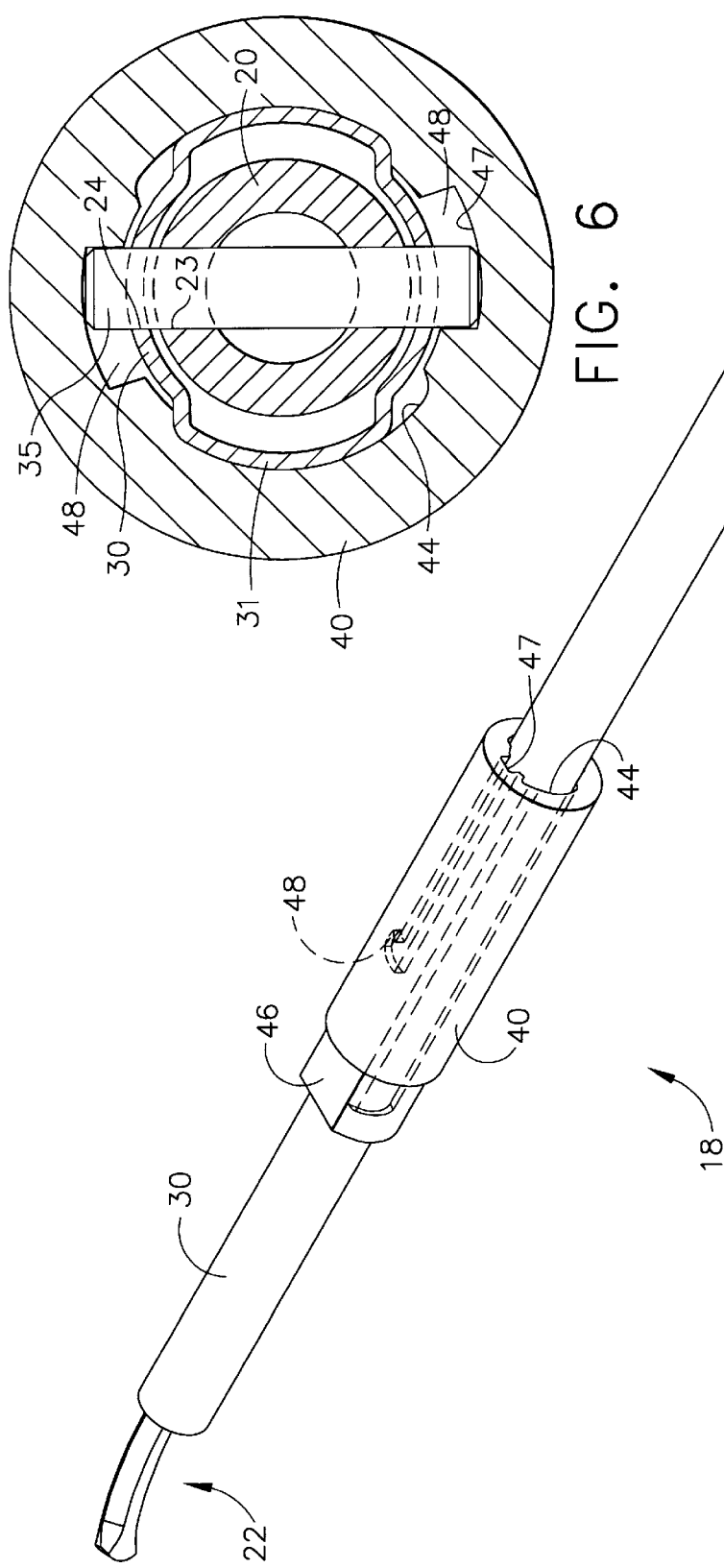
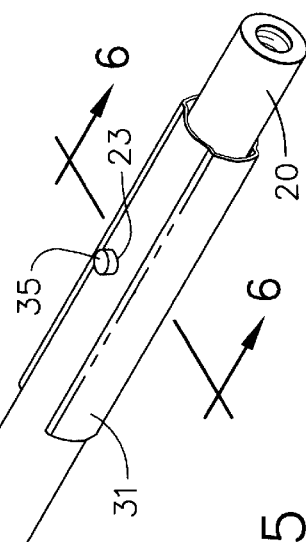

REUSABLE ULTRASONIC SURGICAL INSTRUMENT WITH REMOVABLE OUTER SHEATH

This application is a continuation to the following applications, which are hereby incorporated herein by reference: application Ser. No. 08/808,273 filed Feb. 28, 1997; application Ser. No. 08/808,652, filed Feb. 28, 1997; and application Ser. No. 08/949,161 filed Oct. 10, 1997.

FIELD OF THE INVENTION

The present invention relates, in general, to ultrasonic surgical instruments including removable outer sheaths and, more particularly, to a reusable ultrasonic surgical instruments with an improved removable outer sheath.

BACKGROUND OF THE INVENTION

Ultrasonic surgical instruments, including both hollow core and solid core instruments, are used for the safe and effective treatment of many medical conditions. Ultrasonic surgical instruments, and particularly solid core ultrasonic surgical instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic surgical instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting a transducer mounted at the proximal end of the ultrasonic instrument. The transducer may be constructed of one or more piezoelectric or magnetostrictive elements which are mounted in the instrument handpiece. Vibrations generated by the transducer are transmitted to the surgical end-effector via an ultrasonic waveguide extending from the transducer section to the surgical end-effector.

U.S. Pat. No. 5,810,859 illustrates an ultrasonic surgical instrument for surgical applications wherein the ultrasonic waveguide is fixed within an outer sheath by a pin through a hub. However, the device described in U.S. Pat. No. 5,810,359 is not designed to be disassembled, cleaned, or re-sterilized.

Reusable ultrasonic surgical instruments incorporating removable outer sheaths cleaning and sterilization have been used, for example, Ethicon Endo-Surgery's HARMONIC SCALPEL. The HARMONIC SCALPEL line includes a 10-millimeter diameter reusable ultrasonic surgical instrument which incorporates a removable outer sheath which attaches to the instrument handpiece.

Therefore, it would be advantageous to provide an ultrasonic surgical instrument that may be easily disassembled for cleaning and then reassembled for multiple uses. It would further be advantageous to provide a reusable ultrasonic surgical instrument, which may be assembled before sterilization to reduce instrument assembly time during a surgical procedure. It would further be advantageous to provide an easily assembled reusable ultrasonic surgical instrument sized small enough to fit within an 8-millimeter or smaller trocar. It would further be advantageous to provide an ultrasonic surgical instrument including a removable outer sheath wherein the outer sheath removably and rotateably engages the waveguide to facilitate connection and removal of the waveguide and outer sheath from the handpiece.

SUMMARY OF THE INVENTION

The present invention is directed to an ultrasonic surgical instrument including an improved outer sheath having a first opening at a distal end of the outer sheath, a second opening at a proximal end of the outer sheath, first and second sheath pinholes through the outer sheath proximal to the first opening. An improved sheath according to the present invention further includes a first sheath pin slot extending from the proximal end of the sheath to the first sheath pinhole and a second sheath pin slot extending from the proximal end of the sheath to the second sheath pinhole. An ultrasonic instrument according to the present invention includes an ultrasonic waveguide positioned within the outer sheath wherein the ultrasonic waveguide includes an end-effector extending from the opening of the outer sheath, a waveguide pinhole through the ultrasonic waveguide proximal to the end-effector. An ultrasonic surgical instrument according to the present invention further includes a connector pin, the connector pin extending through the first sheath pinhole, the waveguide pinhole and the second sheath pinhole and an attachment hub surrounding the outer sheath, wherein the attachment hub is slideable over the outer sheath. An ultrasonic surgical instrument according to the present invention may further include a first pin slot on an inner surface of the attachment hub, wherein the connector pin engages the first pin slot when the attachment hub is in its proximal most position.

An alternate embodiment of the present invention is directed to an ultrasonic surgical instrument including an improved outer sheath having a first opening at a distal end of the outer sheath, a second opening at a proximal end of the outer sheath, first and second sheath pinholes through the outer sheath proximal to the first opening. An ultrasonic instrument according to the present invention includes an ultrasonic waveguide positioned within the outer sheath wherein the ultrasonic waveguide includes an end-effector extending from the opening of the outer sheath, a waveguide pinhole through the ultrasonic waveguide proximal to the end-effector. An ultrasonic surgical instrument according to the present invention further includes a connector pin, the connector pin extending through the first sheath pinhole, the waveguide pinhole and the second sheath pinhole and an attachment hub surrounding the outer sheath, wherein the attachment hub is slideable over the outer sheath. An ultrasonic surgical instrument according to the present invention may further include a first pin slot on an inner surface of the attachment hub, wherein the connector pin engages the first pin slot when the attachment hub is in its proximal most position. In a further embodiment of the present invention, the pin slot in the attachment hub is L-shaped with a locking slot at its distal end.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 5 is a perspective view illustrating an alternate embodiment of an ultrasonic surgical instrument according to the present invention with the instrument assembled and the attachment hub in an open position;

FIG. 6 is a magnified cross-sectional view taken through the attachment hub section of the ultrasonic surgical instrument illustrated in FIG. 5, with the attachment hub in its closed position.

DETAILED DESCRIPTION OF THE INVENTION

Figure 1:
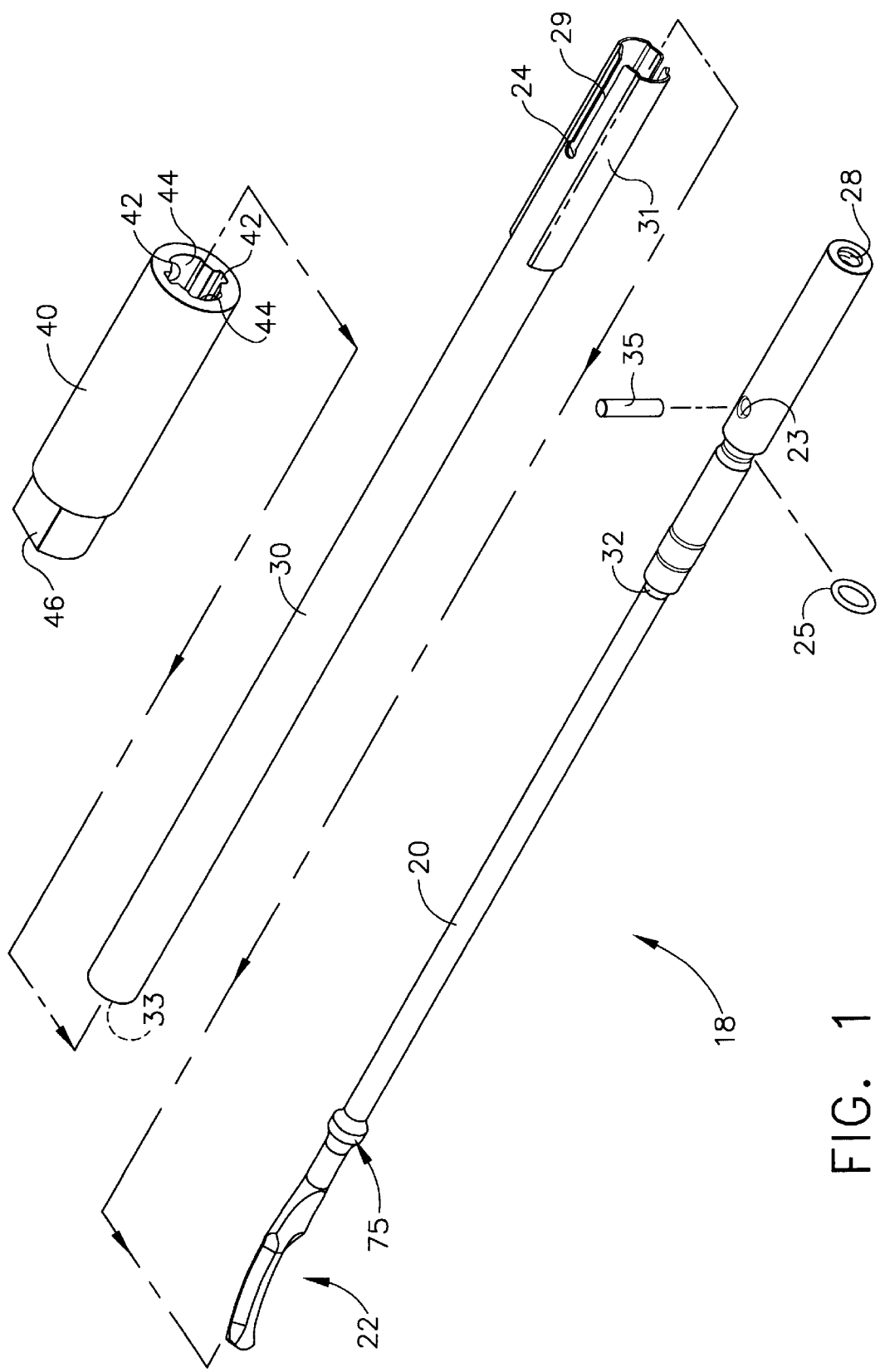
FIG. 1 is an exploded perspective view illustrating an ultrasonic surgical instrument according to the present invention, including an ultrasonic waveguide, outer sheath, slidable hub, and blade end-effector.

FIG. 1 is an exploded perspective view illustrating an ultrasonic surgical instrument 18 according to the present invention In the embodiment of FIG. 1, surgical instrument 18 includes an ultrasonic waveguide 20, an outer sheath 30, an attachment hub 40 and blade end-effector 22. Ultrasonic waveguide 20 includes blade end-effector 22, an acoustic isolation element 75, a recess 32, a waveguide pinhole 23, and an attachment thread 28. Outer sheath 30 includes an opening 33, a sheath pinhole 24, a sheath pin slot 29, and a hub engagement 31. Attachment hub 40 includes a wrench flat 46, a sheath slot 44 and a pin slot 42. A connector pin 35 engages waveguide pinhole 23 and sheath pinhole 24. Connector pin 35 may be fixed in waveguide pinhole 23 by an interference fit or by an adhesive such as, for example, silicone or cyanoacrylate. Alternatively, connector pin 35 may be sized to slide within waveguide pinhole 23. O-ring 25 is sized to fit around ultrasonic waveguide 20 in recess 32 to mechanically isolate ultrasonic waveguide 20 from outer sheath 30. An O-ring 25 and an acoustic isolation element 75 support ultrasonic waveguide 20 within outer sheath 30. Acoustic isolation element 75 is most advantageously positioned at the distal-most vibratory node of ultrasonic waveguide 20. Acoustic isolation element 75 is fixed to ultrasonic waveguide 20 by, for example, molding acoustic isolation element 75 onto ultrasonic waveguide 20 utilizing an injection molding process.

Figure 2:
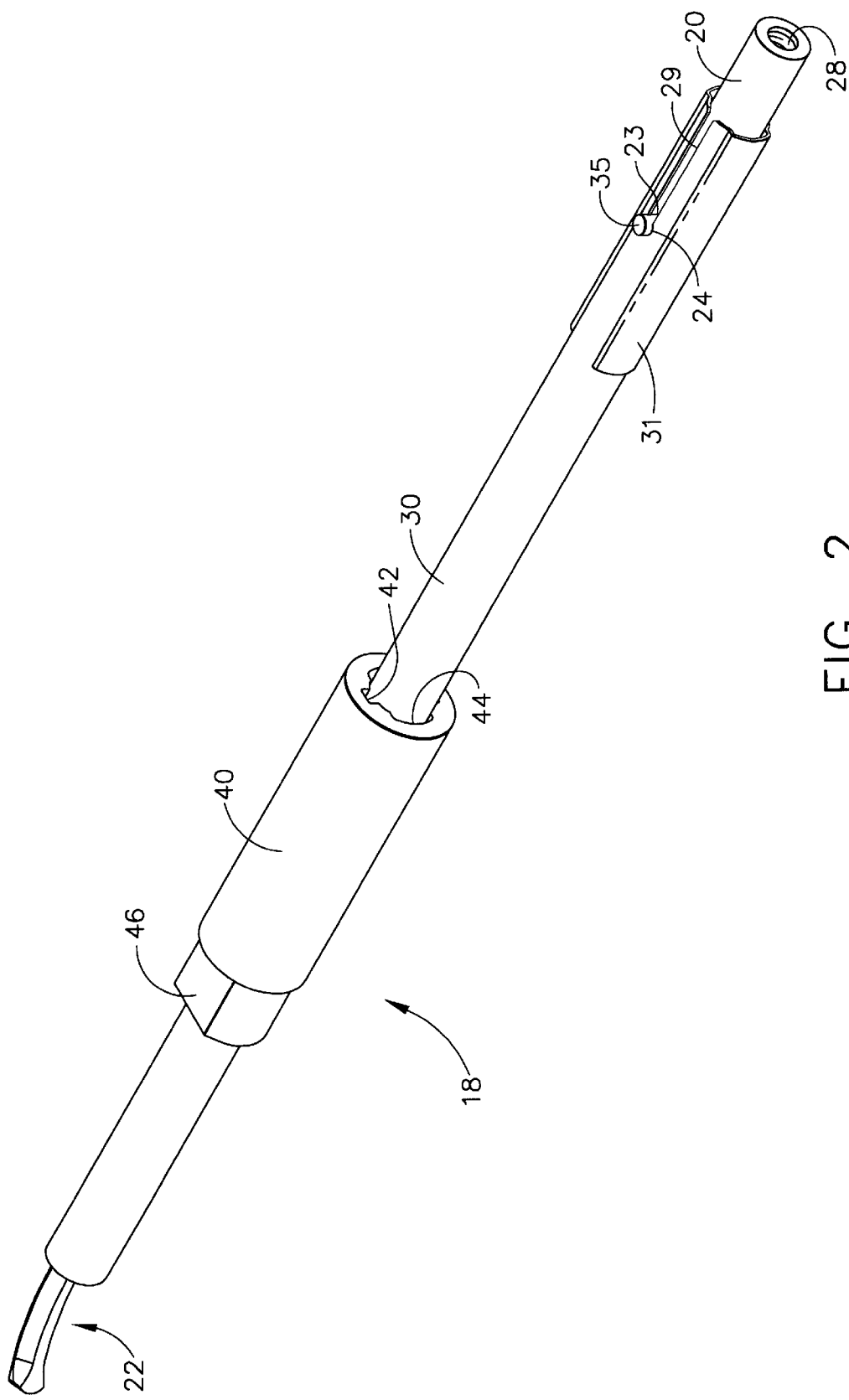
FIG. 2 is a perspective view illustrating the ultrasonic surgical instrument illustrated in FIG. 1 with the instrument assembled and the attachment hub in an open position.

FIG. 2 is a perspective view illustrating the ultrasonic surgical instrument 18 illustrated in FIG. 1 with the instrument assembled. In FIG. 2, attachment hub 40 is in an open position. In FIG. 2, connector pin 35 is positioned in waveguide pinhole 23 and in sheath pinhole 24. When ultrasonic surgical instrument 18 is assembled, ultrasonic waveguide 20 is positioned in outer sheath 30 with blade end-effector 22 projecting from opening 33 in the distal end of outer sheath 30. Ultrasonic waveguide 20 may be fixed in outer sheath 30 by connector pin 35 which is positioned in a waveguide pinhole 23 and a sheath pinhole 24, located at the end of a sheath pin slot 29. Attachment threads 28 are positioned at the proximal end of ultrasonic waveguide 20 to facilitate attachment of ultrasonic surgical instrument 18 to an ultrasonic handpiece (not shown) such as the ultrasonic handpiece shown and desribed in application Ser. No. 08/808,273, filed Feb. 28, 1997, which was previously incorporated herein by reference. As illustrated in FIG. 2, the width of sheath pin slot 29 may be slightly smaller than the width of connector pin 35, requiring that connector pin 35 be forced through sheath pin slot 29 as outer sheath 30 during assembly of ultrasonic instrument 18. Outer sheath 30 is fixed to ultrasonic waveguide 20 by sliding attachment hub 40 proximally over outer sheath 30 which squeezes sheath pin slot 29 and holds connector pin 35 in sheath pinhole 24 preventing outer sheath 30 from disengaging during use. When closed, attachment hub 40 covers connector pin 35, sheath pin slot 29, waveguide pinhole 23, and sheath pinhole 24. Further, since ultrasonic waveguide 20 is rotatably attached to outer sheath 30 and attachment hub 40, wrench flats 46 on attachment hub 40 may be used to attach ultrasonic instrument 18 to an ultrasonic handpiece (not shown).

Figure 3:
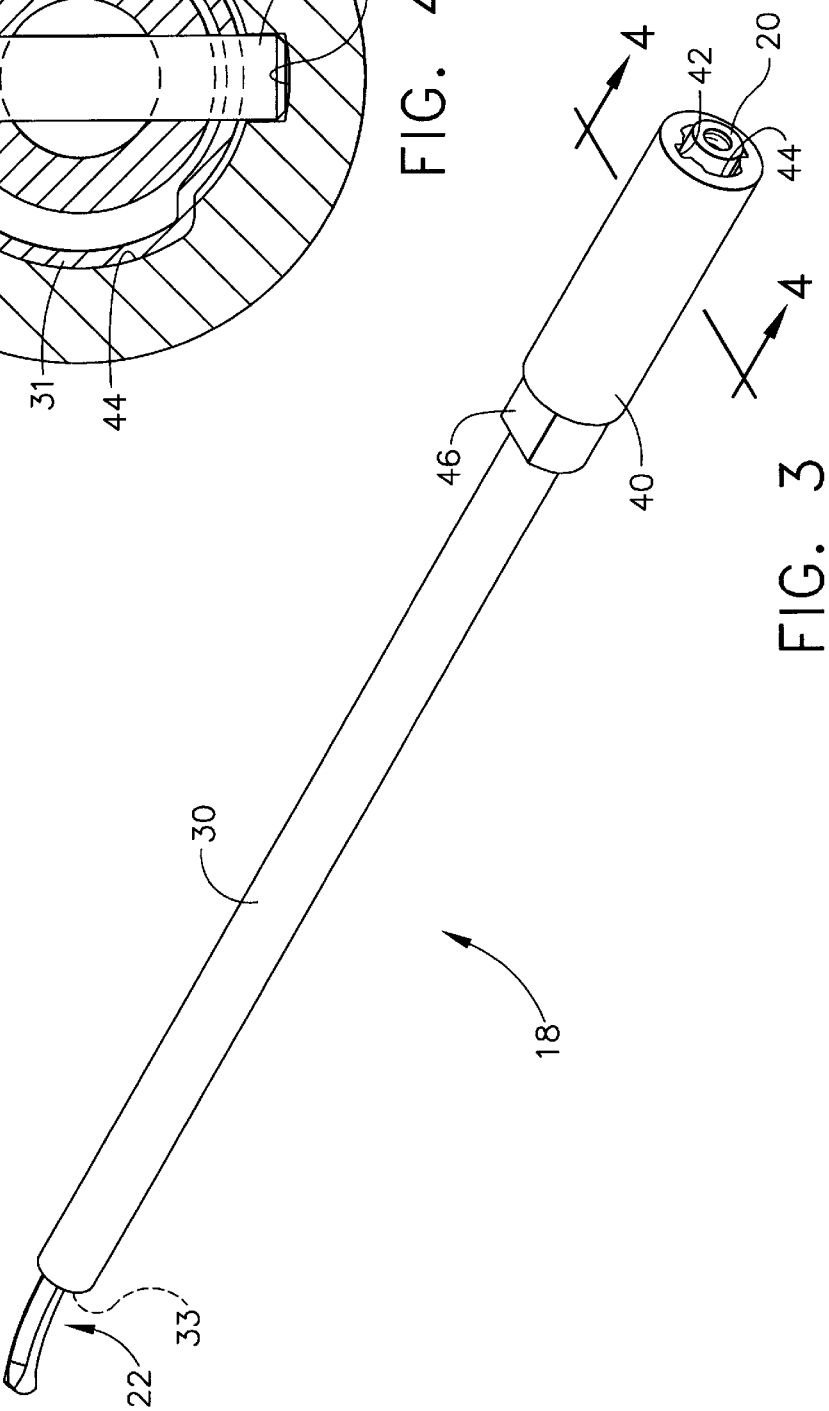
FIG. 3 is a perspective view illustrating the ultrasonic surgical instrument illustrated in FIG. 1 with the instrument assembled and the attachment hub in a closed position.

FIG. 3 is a perspective view illustrating the ultrasonic surgical instrument 18 illustrated in FIG. 1 with the instrument assembled. In FIG. 3, attachment hub 40 is in a closed position. In order to more clearly illustrate the interface between hub 40 and connector pin 35, and outer sheath 30, a cutaway section of the hub region of ultrasonic instrument 18 in FIG. 3 is shown in magnified form in FIG. 4.

Figure 4:
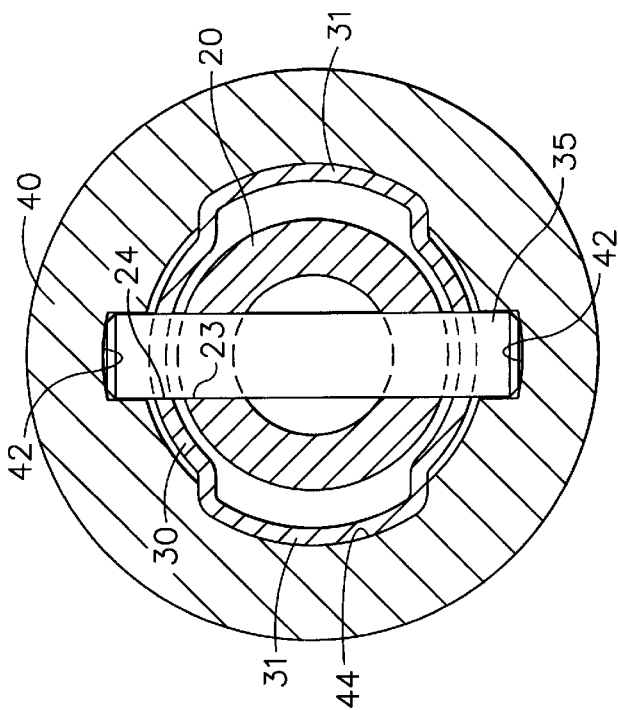
FIG. 4 is a magnified cross-sectional view taken through the attachment hub section as illustrated in FIG. 3.

FIG. 4 is a magnified cross-sectional view taken through the section illustrated as line 4—4 in FIG. 3. Ultrasonic waveguide 20 is seen to have connector pin 35 extending through waveguide pin hole 23, sheath pinhole 24 and into pin slots 42 of attachment hub 40. As illustrated in FIG. 4, hub engagements 31 of ultrasonic waveguide 20 fit into sheath slots 44 of attachment hub 40.

FIG. 5 is a perspective view illustrating an alternate embodiment of an ultrasonic surgical instrument 18 according to the present invention. In FIG. 5, ultrasonic surgical instrument 18 is partially assembled with attachment hub 40 in an open position. In the embodiment of the invention illustrated in FIG. 5, connector pin 35 may be removable from waveguide pinhole 23 to facilitate positioning outer sheath 30 over ultrasonic waveguide 20. When ultrasonic surgical instrument 18 is assembled, ultrasonic waveguide 20 is positioned in outer sheath 30 with blade end-effector 22 projecting from opening 33 at the distal end of outer sheath 30. Connector pin 35 may therein be inserted through sheath pinhole 24 and waveguide pinhole 23. After insertion of connector pin 35 through ultrasonic waveguide 20 and outer sheath 30, attachment hub 40 may be slid proximally over outer sheath 30, engaging connector pin 35 with L-shaped hub slot 47. Attachment hub 40 is then rotated until connector pin 35 seats within locking slot 48. In order to more clearly illustrate the interface between hub 40 and connector pin 35 and outer sheath 30, a cutaway view of the hub region of ultrasonic surgical instrument 18 in FIG. 5 is shown in magnified form in FIG. 6. In the embodiment of the invention illustrated in FIG. 5, ultrasonic surgical instrument 18 further includes hub engagements 31, sheath slots 44 and wrench flats 46.

FIG. 6 is a magnified cross-sectional view taken through the attachment hub section of the ultrasonic surgical instrument illustrated as line 6—6 in FIG. 5. Ultrasonic waveguide 20 is seen to have connector pin 35 extending through waveguide pinhole 23, sheath pinhole 24 and into L-shaped pin slots 47 of attachment hub 40. As illustrated in FIG. 6, hub engagements 31 of waveguide 30 fit into sheath slots 44 of attachment hub 40.

It will be apparent that ultrasonic surgical instruments including the present invention may be used in ultrasonic surgical instruments adapted for open, laparoscopic or endoscopic surgical procedures. It will further be apparent that ultrasonic surgical instruments according to the present invention are particularly adapted for multiple patient use.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:
    an outer sheath wherein said outer sheath comprises;
        a first opening at a distal end of said outer sheath;
        a second opening at a proximal end of said outer sheath;
        first and second sheath pinholes through said outer sheath proximal to said first opening;
        a first sheath pin slot extending from said proximal end of said sheath to said first sheath pinhole;
        a second sheath pin slot extending from said proximal end of said sheath to said second sheath pinhole;
    an ultrasonic waveguide positioned within said outer sheath, said ultrasonic waveguide comprising;
        an end-effector extending from said opening of said outer sheath;
        a waveguide pinhole through said ultrasonic waveguide proximal to said end-effector;
    a connector pin, said connector pin extending through said first sheath pinhole, said waveguide pinhole and said second sheath pinhole; and
    an attachment hub surrounding said outer sheath, wherein said attachment hub is slidable over said outer sheath;
    a first pin slot on an inner surface of said attachment hub, wherein said connector pin engages said first pin slot when said attachment hub is in its proximal most position.

2. An ultrasonic surgical instrument according to claim 1, further comprising:
    an engagement hub protruding from the proximal end of said outer sheath; and
    sheath slots on said inner surface of said attachment hub wherein said engagement hub engages said sheath slot when said attachment hub is in its proximal most position.

3. An ultrasonic surgical instrument according to claim 2, wherein said first and second sheath pin slots have a width which is smaller than the diameter of said connector pin.

4. An ultrasonic surgical instrument according to claim 3, wherein said surgical instrument further comprises at least one acoustic isolation element surrounding said ultrasonic waveguide, whereby said acoustic isolation element separates said ultrasonic waveguide from said outer sheath when said ultrasonic surgical instrument is assembled.

5. An ultrasonic surgical instrument according to claim 4 wherein said attachment hub further comprises wrench flats on the outer surface of said attachment hub.

6. An ultrasonic surgical instrument comprising:
    outer sheath which comprises;
        an opening at the distal end of said outer sheath;
        a sheath pinhole through said outer sheath proximal to said opening;
        a sheath pin slot extending from said sheath pinhole to a proximal end of said outer sheath;
    an ultrasonic waveguide positioned within said outer sheath, said ultrasonic waveguide comprising;
        an end-effector extending from said opening of said outer sheath;
        a waveguide pinhole through said ultrasonic waveguide proximal to said end-effector;
    a connector pin insertable through said sheath pin hole into said waveguide pinhole; and
    an attachment hub surrounding said outer sheath, wherein said attachment hub is slidable over said outer sheath;
    at least one pin slot on an inner surface of said attachment hub, wherein said connector pin engages said pin slot when said attachment hub is in iits most proximal position.

7. An ultrasonic surgical instrument according to claim 6, wherein said outer sheath further comprises:
    hub engagements protruding from the proximal end of said outer sheath; and
    said attachment hub further includes hub sheath slots on said inner surface of said attachment hub wherein said hub engagements engage said hub sheath slots when said attachment hub is in its most proximal position.

8. An ultrasonic surgical instrument according to claim 7, wherein said sheath pin slot has a width which is smaller than the diameter of said connector pin.

9. An ultrasonic surgical instrument according to claim 8, wherein said surgical instrument further comprises at least one acoustic isolation element surrounding said ultrasonic waveguide, whereby said acoustic isolation element separates said ultrasonic waveguide from said outer sheath when said ultrasonic surgical instrument is assembled.

10. An ultrasonic surgical instrument according to claim 9 wherein said attachment hub further comprises wrench flats on the outer surface of said attachment hub.

11. A sheath for an ultrasonic surgical instrument, wherein said sheath comprises:
    an outer sheath;
    a first opening at a distal end of said outer sheath;
    a second opening at a proximal end of said outer sheath;
    first and second sheath pinholes through said outer sheath proximal to said first opening;
    a first sheath pin slot extending from said proximal end of said sheath to said first sheath pinhole;
    a second sheath pin slot extending from said proximal end of said sheath to said second sheath pinhole.

12. A sheath for an ultrasonic surgical instrument according to claim 11, further comprising:
    an attachment hub surrounding said outer sheath, wherein said attachment hub is slidable over said outer sheath; and
    a first pin slot on an inner surface of said attachment hub.

13. A sheath for an ultrasonic surgical instrument according to claim 12, said sheath further comprising:
    a hub engagement protruding from the proximal end of said outer sheath; and
    sheath slots on said inner surface of said attachment hub wherein said attachment hub engages said sheath slot when said attachment hub is in its proximal most position.

14. An ultrasonic surgical instrument according to claim 13, wherein said first and second pin slots have a width which is smaller than the diameter of said connector pin.

15. An ultrasonic surgical instrument according to claim 14, wherein said surgical instrument further comprises at least one acoustic isolation element surrounding said ultrasonic waveguide, whereby said acoustic isolation element separates said ultrasonic waveguide from said outer sheath when said ultrasonic surgical instrument is assembled.

16. An ultrasonic surgical instrument according to claim 15 wherein said attachment hub further comprises wrench flats on the outer surface of said attachment hub.

17. An ultrasonic surgical instrument comprising:
   an outer sheath wherein said outer sheath comprises;
      a first opening at a distal end of said outer sheath;
      a second opening at a proximal end of said outer sheath;
      first and second sheath pinholes through said outer sheath proximal to said first opening;
   an ultrasonic waveguide positioned within said outer sheath, said ultrasonic waveguide comprising;
      an end-effector extending from said opening of said outer sheath;
      a waveguide pinhole through said ultrasonic waveguide proximal to said end-effector;
   a connector pin, said connector pin extending through said first sheath pinhole, said waveguide pinhole and said second sheath pinhole; and
   an attachment hub surrounding said outer sheath, wherein said attachment hub is slidable over said outer sheath;
   a first pin slot on an inner surface of said attachment hub, wherein said connector pin engages said first pin slot when said attachment hub is in its proximal most position.

18. An ultrasonic surgical instrument according to claim 17, further comprising:
   an engagement hub protruding from the proximal end of said outer sheath; and
   hub sheath slots on said inner surface of said attachment hub wherein said engagement hub engages said sheath slot when said attachment hub is in its proximal most position.

19. An ultrasonic surgical instrument according to claim 18, wherein said first and second hub pin slots are L shaped, with a locking slot at their distal end.

20. An ultrasonic surgical instrument according to claim 19, wherein said surgical instrument further comprises at least one acoustic isolation element surrounding said ultrasonic waveguide, whereby said acoustic isolation element separates said ultrasonic waveguide from said outer sheath when said ultrasonic surgical instrument is assembled.

21. An ultrasonic surgical instrument according to claim 20 wherein said attachment hub further comprises wrench flats on the outer surface of said attachment hub.

* * * * *